(12) United States Patent
Reed et al.

(10) Patent No.: US 9,304,071 B2
(45) Date of Patent: Apr. 5, 2016

(54) SYSTEM AND METHOD FOR TESTING OF MICRO-SIZED MATERIALS

(71) Applicant: The Government of the United States of America, as represented by the Secretary of the Navy, Washington, DC (US)

(72) Inventors: Allen Hagerman Reed, Bay St. Louis, MS (US); Guoping Zhang, Amherst, MA (US); Hang Yin, Baton Rouge, LA (US); David C. Young, Long Beach, MS (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/620,515

(22) Filed: Feb. 12, 2015

(65) Prior Publication Data

US 2015/0160107 A1    Jun. 11, 2015

Related U.S. Application Data

(63) Continuation of application No. 13/616,163, filed on Sep. 14, 2012, now Pat. No. 8,984,957.

(60) Provisional application No. 61/592,276, filed on Jan. 30, 2012.

(51) Int. Cl.
*G01N 3/00* (2006.01)
*G01N 3/08* (2006.01)
*G01N 3/06* (2006.01)

(52) U.S. Cl.
CPC .................. *G01N 3/08* (2013.01); *G01N 3/068* (2013.01); *Y10T 29/49826* (2015.01)

(58) Field of Classification Search
CPC ...... G01N 3/068; G01N 3/08; Y10T 29/49826
USPC ...................... 73/800, 818, 862.624
See application file for complete search history.

(56) References Cited

U.S. PATENT DOCUMENTS

| | | | | |
|---|---|---|---|---|
| 5,517,861 A * | 5/1996 | Haas | ...................... | G01N 3/068 356/237.1 |
| 5,606,132 A * | 2/1997 | Simpson | ................... | G01B 5/30 73/768 |
| 6,487,914 B1 * | 12/2002 | Hodge | ................... | G01B 11/16 73/800 |
| 6,711,941 B2 * | 3/2004 | Braithwaite | ............. | G01N 3/08 73/53.01 |
| 6,825,996 B2 * | 11/2004 | Watanabe | .......... | G01N 21/8803 356/237.1 |
| 8,776,611 B2 * | 7/2014 | Sangel | ................ | E21B 47/0006 405/188 |

(Continued)

FOREIGN PATENT DOCUMENTS

| | | |
|---|---|---|
| KR | 1020080074625 A | 8/2008 |
| KR | 1020110131570 A | 12/2011 |
| WO | 2005090942 A1 | 9/2005 |

OTHER PUBLICATIONS

Radmacher, M. et al, (1995) Imaging Soft Samples with the Atomic Force Microscope: Gelatin in Water and Propanol, Biophysical Journal, vol. 69, pp. 264-270.

(Continued)

*Primary Examiner* — Max Noori

(57) ABSTRACT

Apparatus and methods for testing sediment submerged in liquid and manufacturing the apparatus.

6 Claims, 10 Drawing Sheets

(56) References Cited

U.S. PATENT DOCUMENTS

2006/0096385 A1  5/2006  Wenski
2011/0214506 A1  9/2011  Khoury et al.

OTHER PUBLICATIONS

Markidou, A., et al (2005) Soft-materials elastic and shear moduli measurement using piezoelectric cantilevers, Review of Scientific Instruments 76, 064302.

Ishiguro, T., et al (2008) the Localization of Phytate in Tofu Curd Formation and Effects of Phytate on Tofu Texture, Journal of Food Science vol. 73, No. 2, pp. C67-C71.

Righetti, R., et al (2004) The Feasibility of using elastography for imaging the poisson's ratio in porous media, Ultrasound in Medicine & Biology, vol. 30, No. 2, pp. 215-228.

Rae, P.J., Dattelbaum, D.M., (2004) The properties of poly (tetrafluoroethylene) (PTFE) in compression, Science Direct, Polymer 45 pp. 7615-7625.

Samani, A, et al (2007) An inverse problem solution for measuring the elastic modulus of intact ex vivo breast tissue tumours, Physics in Medicine and Biology, vol. 52, pp. 1247-1260.

Zin-Sheng Liu, et al (2004) Effect of selective thermal denaturation of soybean proteins on soymilk viscosity and tofu's physical properties, Food Research International vol. 37, pp. 815-822.

Leroux, Pierre (2010) Nanovea, Compression Measurement of Foam with Microindentation, 6 Morgan, Ste 156, Irvine, CA 92618.

Ashby, M., and Cebon, D.(2002) New approaches to Materials Education, The CES 4 EduPack,course, Cambridge, UK.

International Search Report, PCT/US2012/063254, Korean Intellectual Property Office Mar. 13, 2013.

* cited by examiner

SYSTEM AND METHOD FOR TESTING OF MICRO-SIZED MATERIALS

CROSS-REFERENCE

This Application is a continuation of and claims the benefit of priority under 35 U.S.C. §120 based on U.S. Non-Provisional patent application Ser. No. 13/616,163 filed on Sep. 14, 2012, which is a non-provisional application claiming priority to Provisional U.S. Patent Application No. 61/592,276 filed on Jan. 30, 2012, under 35 USC 119(e), both of which are incorporated by reference into the present disclosure in their entirety.

BACKGROUND

The embodiments disclosed herein relate generally to compression or tension testing of flocculated sediments, an aggregate mixture of clay minerals and biopolymers, referred to herein alternatively as "floc" or "sediment". To test a floc, it should remain saturated and submerged in the formation solution. The floc must be easily isolated from other flocs for single floc geotechnical compression tests that can be made relatively rapidly on a large number of samples. A device to test a floc should have minimal and quantifiable frictional resistance to motion, minimal and quantifiable cantilever effect, and minimal, known, or quantifiable compressional resistance of the manipulator tips. Fine-grained sediment transport, deposition and consolidation of soft sediments is determined, in part, by a complex relationship between sediment makeup and geotechnical properties of clay-aggregates. Compression tests on soft sediment grains that are comprised of clay and polymers can help to better understand how contact interactions could alter the aggregate properties and influence sediment processes of transport, deposition, and consolidation in estuarine and nearshore littoral environments. Compression tests can provide data that can be incorporated into numerical models, which can be used to predict sediment transport processes. In order to determine the compressive strength of clay aggregates, a highly sensitive load cell and mechanism to hold the small specimens (~0.5 to 2 mm in diameter) in a controlled vertical plane are needed. Such a device would require a fluid receptacle within which the specimen is submerged and resting on a sample plate. The sample plate could be manipulated upward, via a stepper motor-driven lift that could push the specimen at a controlled and specified rate into the "punch" that could be connected to a load cell. The load cell could transfer the information to a computer that could quantify the force required to deform the specimen. Such a device could be used in nano/micro mechanical testing of individual flocs, or other small particles, in sizes that range from approximately 10 to approximately 5000 microns. The device could facilitate compression tests of flocs that are comprised of clay and polymers mixed in fresh or salt water for which the pH, or other chemistry, varies. The device could also facilitate imaging the deformation process in real-time, and could use that capability to correlate the floc compressive deformation process by generating a graphical representation of a force-displacement (i.e., compression) curve. The compression data could then be readily used to address the influence of contact interactions between flocs and deformation of those flocs in discrete element models of sediment transport.

What is needed is an environmental cell for nano/micro mechanical and biomechanical testing to facilitate compression or tension tests of soft sediment aggregates that include clay and polymers mixed in fresh and salt water and which are retained in a liquid of the same salinity, alternatively for testing biological materials such as, for example, blood cells, virus, and bacteria, and also gels, foams, rubbers, surface coatings, and food. Currently, compression tests are not conducted on small aggregates that are comprised of soft, low-strength, materials. Also, there are no technologies available that can quantify the Young's modulus of these grains. Currently, these measurements are not made on soft, low-strength, materials.

SUMMARY

This system and method of the present embodiment can enable testing of similar specimens in aqueous environments, such as food materials, cosmetics, chemicals, etc. The apparatus and methods of the present embodiment can provide for nano/micro mechanical testing of micro-sized materials submerged in liquid, facilitating specimen preparation and installation, and can provide hydrated materials. The apparatus can include cell walls with optical magnifying lenses so that the micro-sized specimens can be viewed without the aid of a microscope. For example, compression or tension tests of soft sediment aggregates and biological materials can be performed. The apparatus may have no frictional resistance between the parts that move to compress the flocs. The water bath can be maintained at a specific elevation and, because the water level or "the buoyant force" can be sensed by the load cell on, for example, but not limited to, an AGILENT TECHNOLOGIES® T150 Nano UTM. The UTM, or other similar device, includes, but is not limited to including, a frame that holds a load cell, a base plate, and a stepper motor that can move the base plate towards the load cell, and a computer that can transfer data from the load cell to a storage medium, reproducible and discernible results can be achieved. The 10× magnifiers can locate flocs and position them between the "compression punch" and "sample holder". The clear imaging window can enable photography and movies of the floc during the compression test. A single floc or other material can be submerged in fluids of varied ionic strength and pH. At least two 10×, for example, viewing windows can be positioned at preselected angles to facilitate sample loading and alignment of small particles. The apparatus can enable real-time movies of compression tests to be captured. The apparatus can enable testing of compression in aqueous systems with, for example, but not limited to, an AGILENT TECHNOLOGIES® NanoUniversal Loading Frame and similar devices from other companies. The apparatus can be used to determine the fate and survivability of river-borne aggregates in estuarine and littoral zone waters. Further, the device can be used to quantify Young's moduli of small granular materials. The data produced by the device can be used to make predictions of grain interactions associated with sediment transport, specifically sediment transport of fine-grained sediment aggregates. The data may also be used to address the strength of similarly sized composite materials with low strength, such as beads, elastomers, food products, and cosmetics.

An environmental cell can be manufactured for nano/micro mechanical testing of micro-sized materials submerged in liquid, facilitating specimen preparation and installation, and providing hydrated materials. For example, compression or tension tests of soft sediment aggregates and biological materials can be performed. The apparatus can determine the compressive strength, elastic moduli or Young's moduli, of soft, sediment aggregates comprised of clay or clay and biopolymers. The apparatus can further collect data on clay aggregates as well as food material (for example, but not limited to, tofu and gelatin) which has similar compressive strength.

The environmental cell can be coupled to a load cell (for example, but not limited to, Agilent UTM-150 with 50 nN force resolution). The load cell can be contained in a frame, inverted in the present embodiment, and can have a stepper motor. The environmental cell can be placed on a stage that is connected to the stepper motor, the stage also being connected to the environmental cell, the environmental cell containing the fluid and the sediment aggregate. The sediment aggregate is then positioned to contact the punch pin that is connected to the load cell, so that as the load cell is moved upward at a computer controlled rate (the strain rate), the load cell can detect the force of the sediment aggregate during displacement of the environmental cell. During this time period, a video camera collects images of the sediment aggregate, stills that can be used to produce a video. The displacement of the environmental cell is time-synched with the force determination and then this information is plotted as a force curve (force vs. displacement) in real-time on the load cell computer.

DETAILED DESCRIPTION

The problems set forth above as well as further and other problems are solved by the present teachings. These solutions and other advantages are achieved by the various embodiments of the teachings described herein below.

Figure 1:
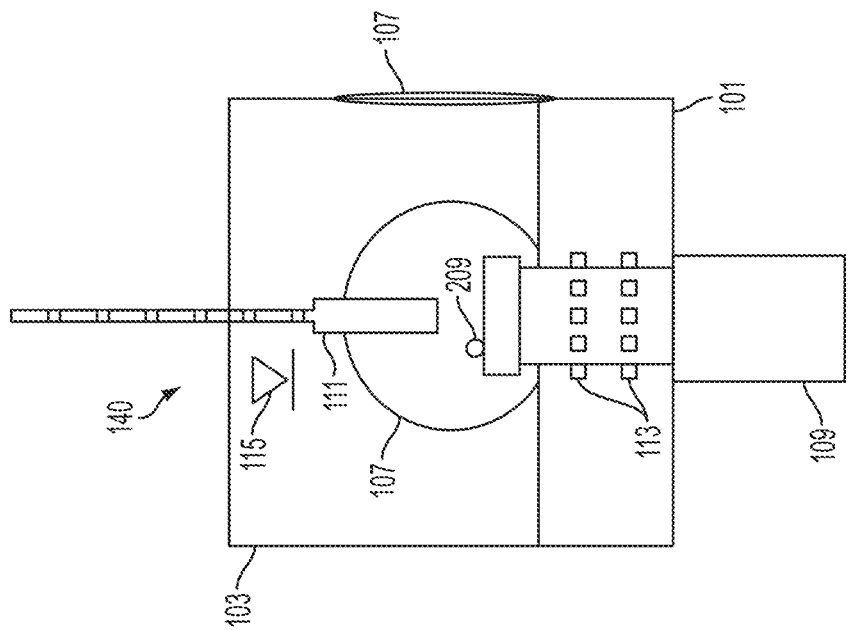
FIG. 1 is a schematic diagram of the apparatus of the present embodiment.
Figure 1:
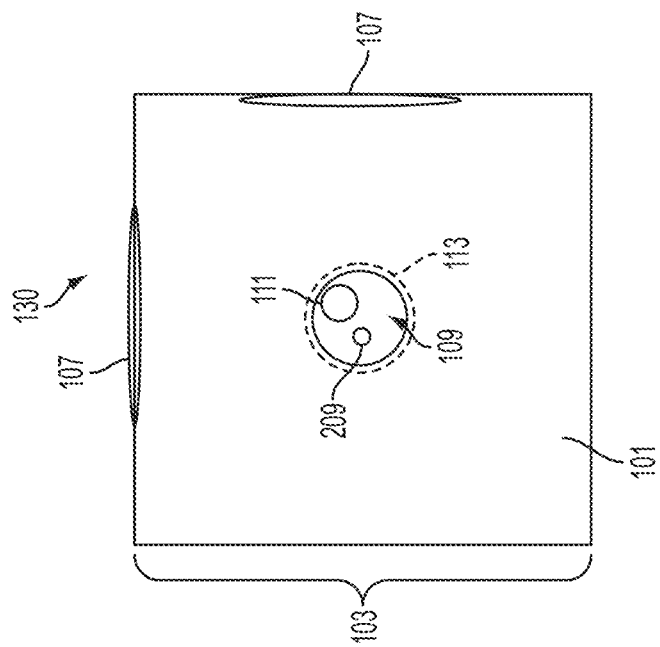

Referring now to FIG. 1, apparatus 100, viewed from top view 130 and side view 140, can include, but is not limited to including, base plate 101 made from, for example, DELRIN®, imaging window plate 103 made from, for example, acrylic, side plates made from, for example, acrylic, magnifying window magnifying lens 107 made of, for example, but not limited to, glass, sample holder 109 made from, for example, stainless steel, O-rings 113 made from, for example, butyl nitrile rubber, and compression punch 111 made from, for example, stainless steel. Fluid bath 115 can hold enough supernatant fluid to maintain the constant chemistry of the hydrated materials during the test. Apparatus 100 can provide a means to hold, locate, and maintain properties of aggregate during compression tests of soft materials in an aqueous environment, and can automatically compute a force-displacement curve. This can enable tests of compressive strength while enabling the operator to view the placement of the floc and deformation of the floc through magnified lenses 107 and to capture images of the deformation process with a microscope through picture imaging window 103. The determination of the elastic moduli, among other material properties, can be computed based on the force-displacement curve and the particle size information.

Apparatus 100 can allow fluid to be maintained with the sample, which can be emplaced on a surface mounting rod, also referred to herein as sample support rod, 109 and viewed through 10× magnifying windows 103, which can render apparatus 100 suitable for viewing micrometer-sized objects. The sample material can then be compressed under a controlled load and viewed with a microscope at high resolution/magnification so as to capture information on strain and deformation. Apparatus 100 can be coupled with, for example, but not limited to, a device to perform nanomechanical testing, for example, AGILENT TECHNOLOGIES® UTM T150, which can be used to measure compressive strength and therefore extend the capabilities from simple tensile strength tests.

Figure 2:
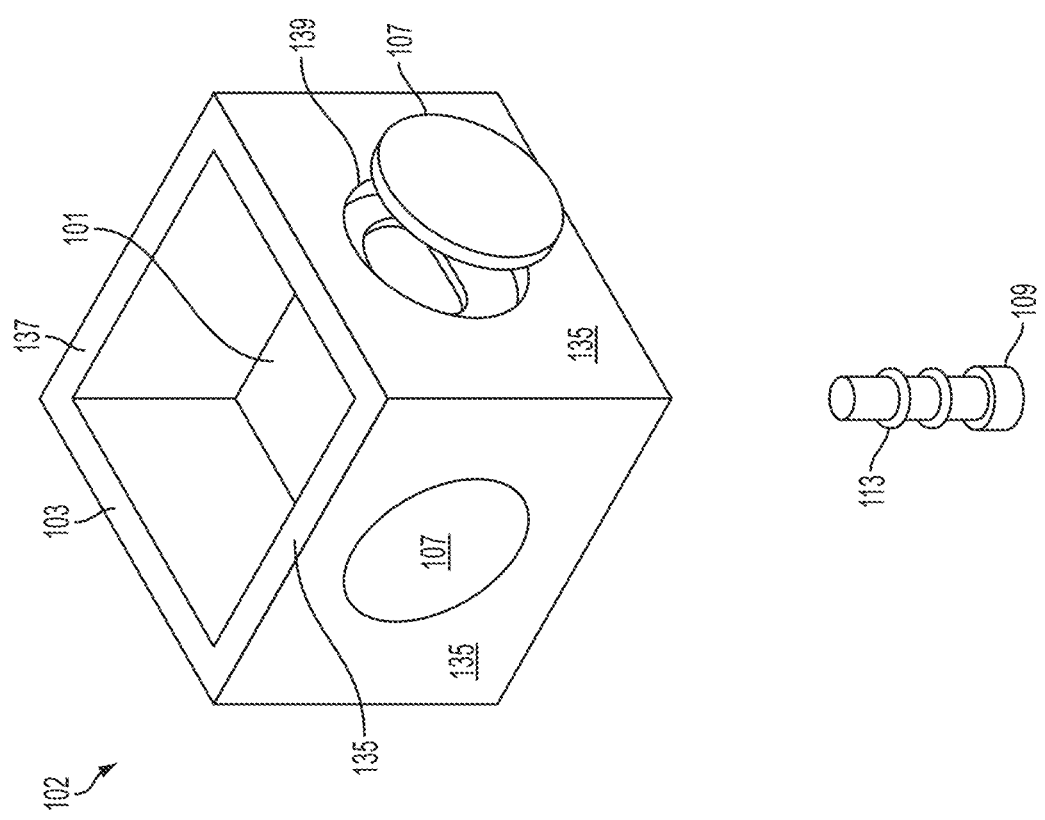
FIG. 2 is a CAD-drawing of the apparatus of the present embodiment.

Referring now to FIG. 2, environmental cell 102 of apparatus 100 (FIG. 1) can include blank side plates 137 and lens side plates 135 made of, for example, but not limited to, acrylic, that are connected to each other, for example, but not limited to, by gluing using, for example, but not limited to, acrylic solvent. Lens side plates 135 can be made of, for example, but not limited to, acrylic which can measure, but is not limited to measuring, approximately two inches in height, approximately 2.46 inches in width, and approximately 0.23 inches in width. Lens side plates 135 can include magnifying lens 107, for example, but not limited to, 10× magnifying lenses, made out of, for example, but not limited to, glass, which can be fixed in place, for example glued, using, for example, but not limited to, 3M® 5200 adhesive sealant. Lens side plates 135 can also include lens recesses 139. can also include base plate 101 such as, for example, but not limited to, a DELRIN® plate glued to blank side plates 137 and lens side plates 135 using, for example, but not limited to, 3M® 5200 adhesive sealant. can also include for example, but not limited to, No. 2006 O-rings 113, and sample support rod 109 made from, for example, but not limited to, 316 stainless steel. The configuration and sizes of blank side plates 137 and lens side plates 135 can be different from the depicted embodiment.

Figure 3:
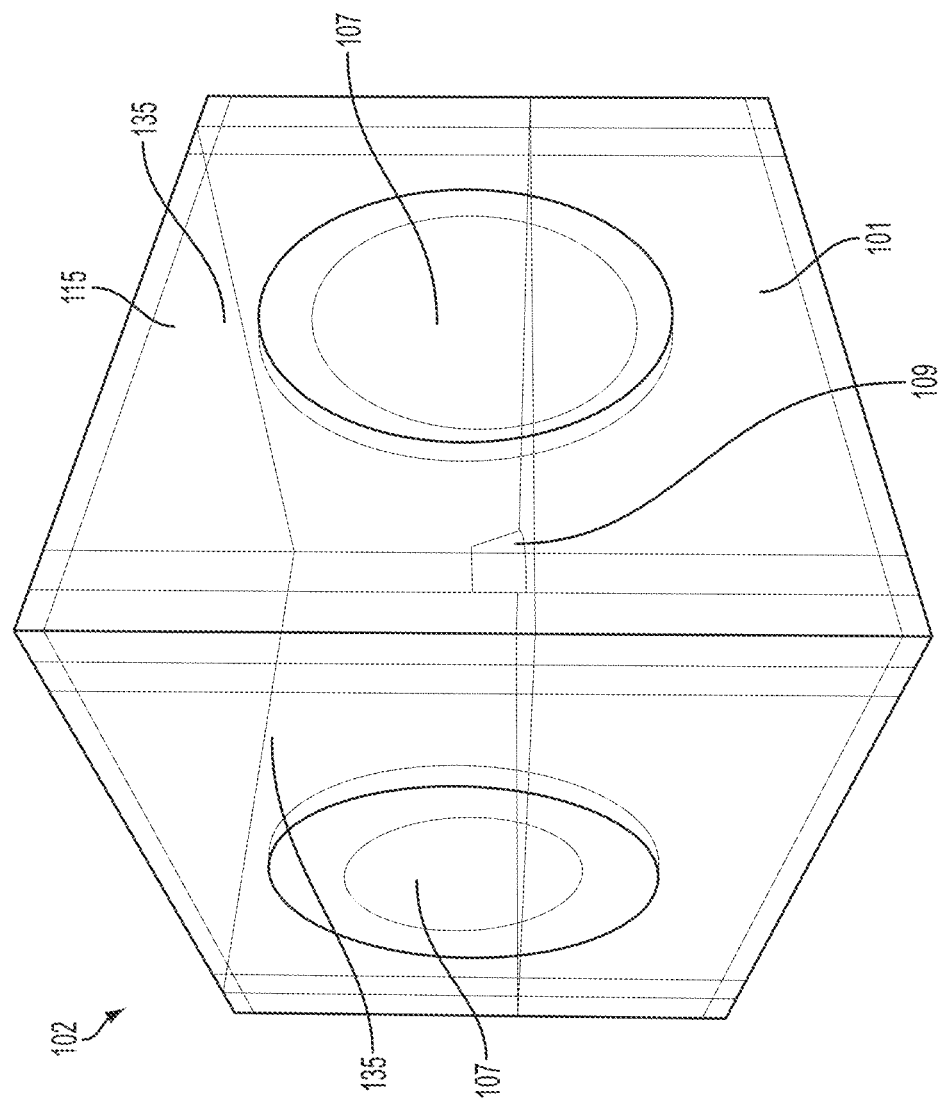
FIG. 3 is a virtual photographic representation of the apparatus of the present embodiment.

Referring now to FIG. 3, environmental cell 102 is shown in use including fluid bath 115. Lens side plates 135, 10× magnifying windows 107, DELRIN® base plate 101, and sample support rod 109 are also shown.

Figure 4:
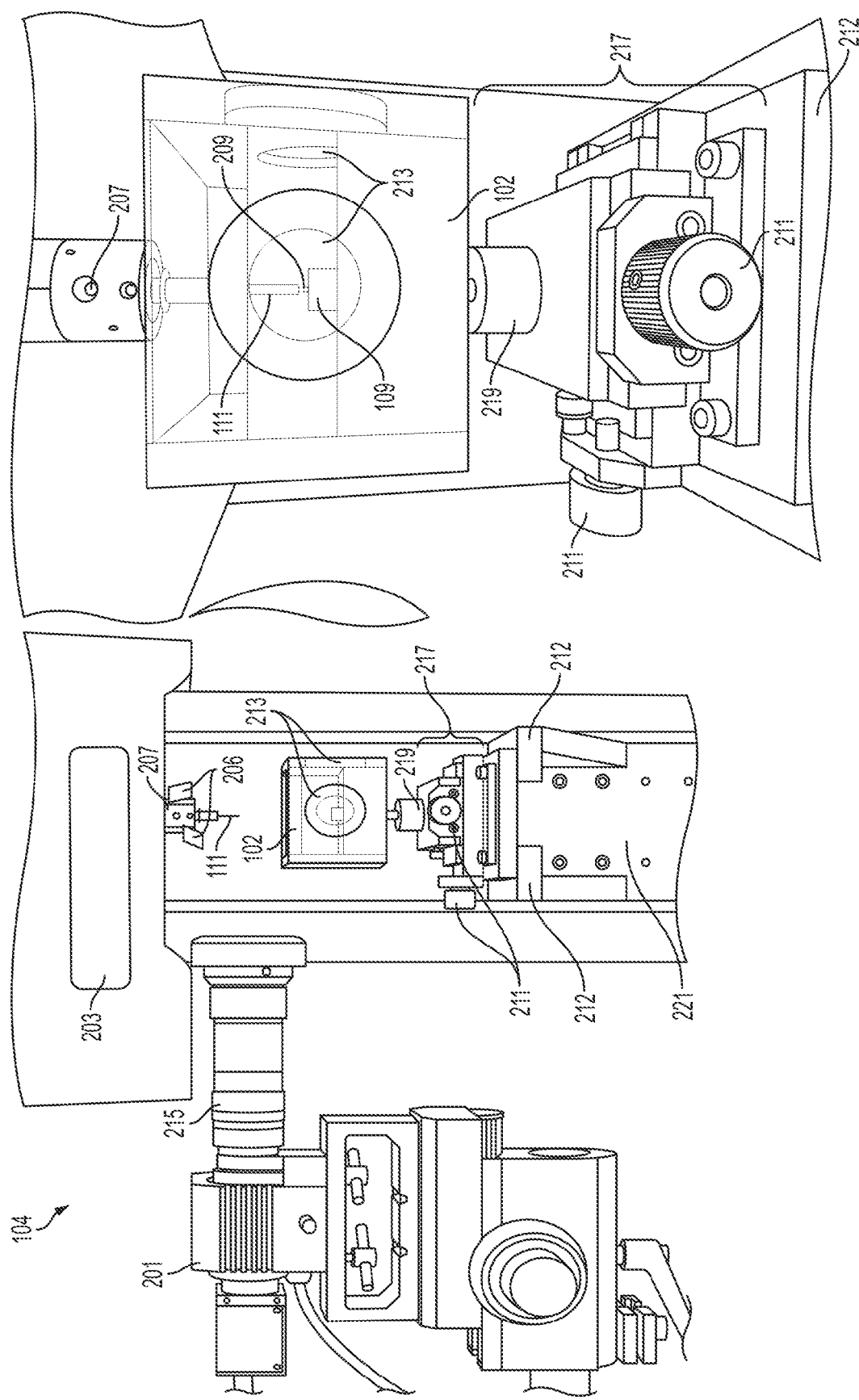
FIG. 4 is a photographic representation of the apparatus of the present embodiment as it would be coupled to the load cell device and positioned with respect to the image capture system.

Referring now to FIG. 4, embodiment 104 of environmental cell 102 (FIG. 1) is shown from two points of view. Embodiment 104 can include video camera 201 that is attached to microscope 215 and load cell device 203 in an inverted position, compression punch 111, flags 206 to maintain load cell in parked position, load cell 207, clay floc 209, stage manipulators 211, magnifying view windows 213 to facilitate sample loading, orienting, and aligning with respect to compression punch 111, by reorienting micromanipulator stage 217 with stage manipulators 211 to move environmental cell 102 that is connected to stage mount 219, and belt-drive 221 that can migrate stepper motor plate 212 and micromanipulator stage 217 upwards. During this process, as belt-drive 221 moves stepper motor plate 212, micromanipulator stage 217, and environmental cell 102 upwards, pre-aligned floc 209 can interact with compression punch 111 and load cell 203 to transfer force and displacement data to a load cell computer (not shown). Simultaneously, video camera 201 can capture imagery of the floc 209 deformation and can transport the images to an image processing computer (not shown).

Figure 5:
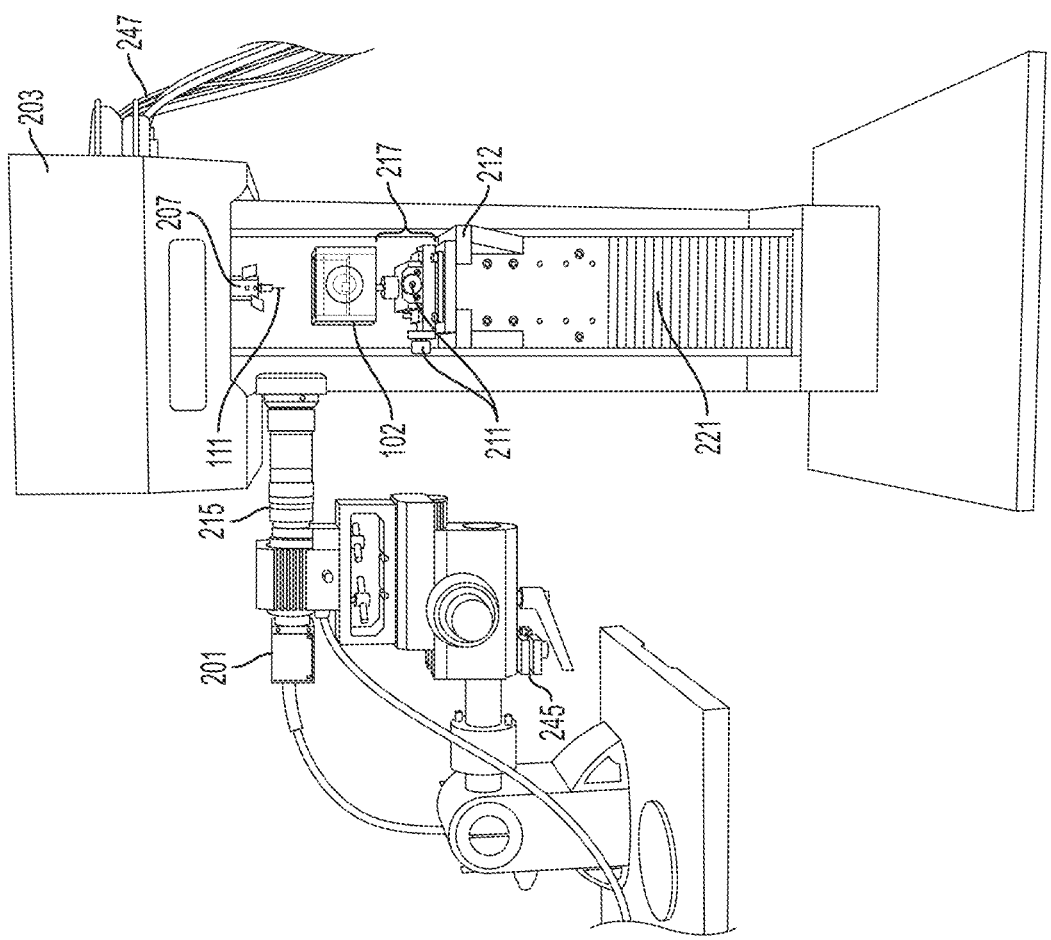
FIG. 5 is a photographic representation of the apparatus of the present embodiment as it would be coupled to the load cell device and positioned with respect to the image capture system with indication that the compression test data and the images are transferred to different computers.

Referring now to FIG. 5, video camera 201 having connecting cables 245, connecting video camera to image processing computer (not shown) is shown with respect to the load cell device 203, for example, but not limited to, AGILENT TECHNOLOGIES® UTM150, and principal components of load cell 207, compression punch 111, environmental cell 102, micromanipulator stage 217, stage manipulators 211, stepper motor plate 212, and belt-drive 221 that can migrate micromanipulator stage 217 and environmental cell 102 upwards. Load cell 203 can collect data that are transferred to the data processing load cell computer (not shown); video camera 201 can transfer data to an image processing computer (not shown).

Figure 6:
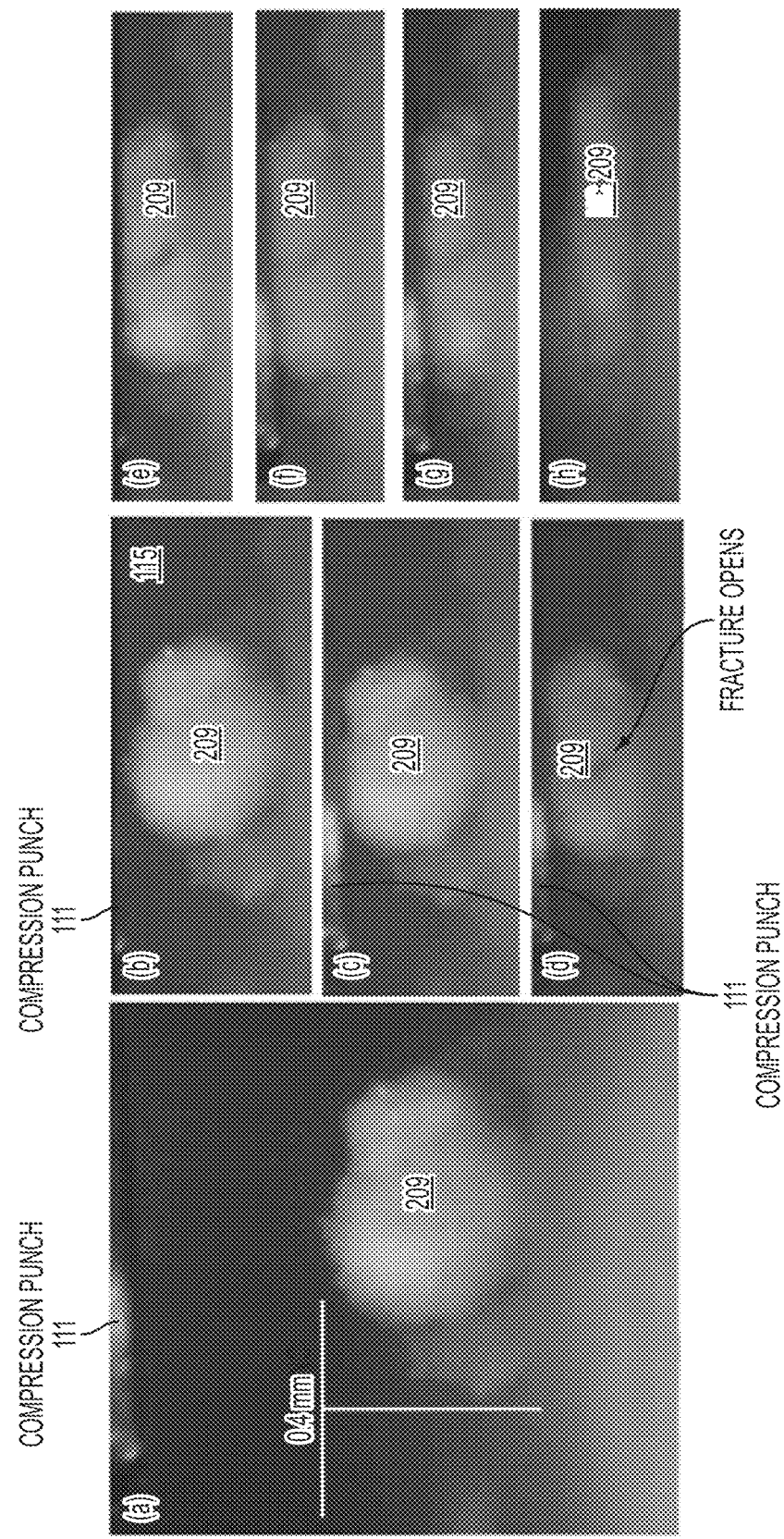
FIG. 6 is a photographic representation of the flocs under compression during various phases of the displacement during the compression test.

Referring now primarily to FIG. 6, compression/deformation of floc 209 is shown in a series of images ((a)-(h)) that capture the vertical migration of environmental cell 102 (FIG. 3) as sample support rod 109 (FIG. 3) drives floc 209 into compression punch 111. These images correspond to FIG. 7, the graph of load versus compression. During this process, floc 209 is submerged in the supernatant fluid within the environmental cell 102, which can migrate upward to push floc 209 (and sample support rod 109) through supernatant fluid 115 and, eventually, into contact with floc 209 to the end of the test where environmental cell 102 (FIG. 3) and sample support rod 109 (FIG. 3) can reverse migration to unload floc 209, which remains deformed (image (h) in FIG. 6).

Figure 7:
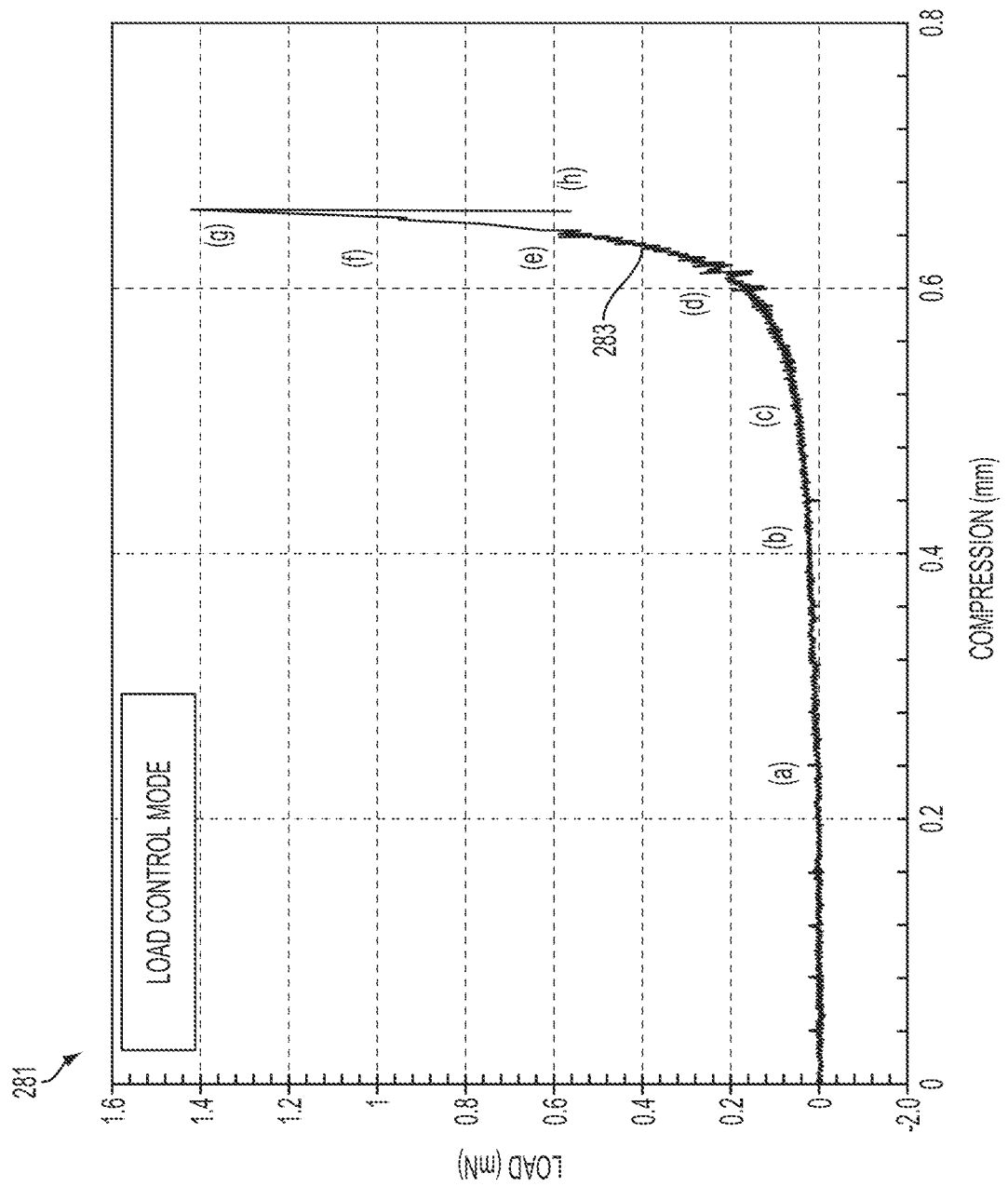
FIG. 7 is a graphical depiction of compressive strength of clay/organic matter mix that relates the images of FIG. 6 to locations on the graph.

Referring now to FIG. 7, graph 281 of load versus compression is shown for the compression of gray-green aggregate made of clay, e.g. illite, and organic matter, e.g. guar, mixed in salt-water of neutral pH. The graph shows the load in mN and compressive displacement of the load cell. Letters displayed along curve 283 correspond to images (a)-(h) in FIG. 6.

Figure 8A:
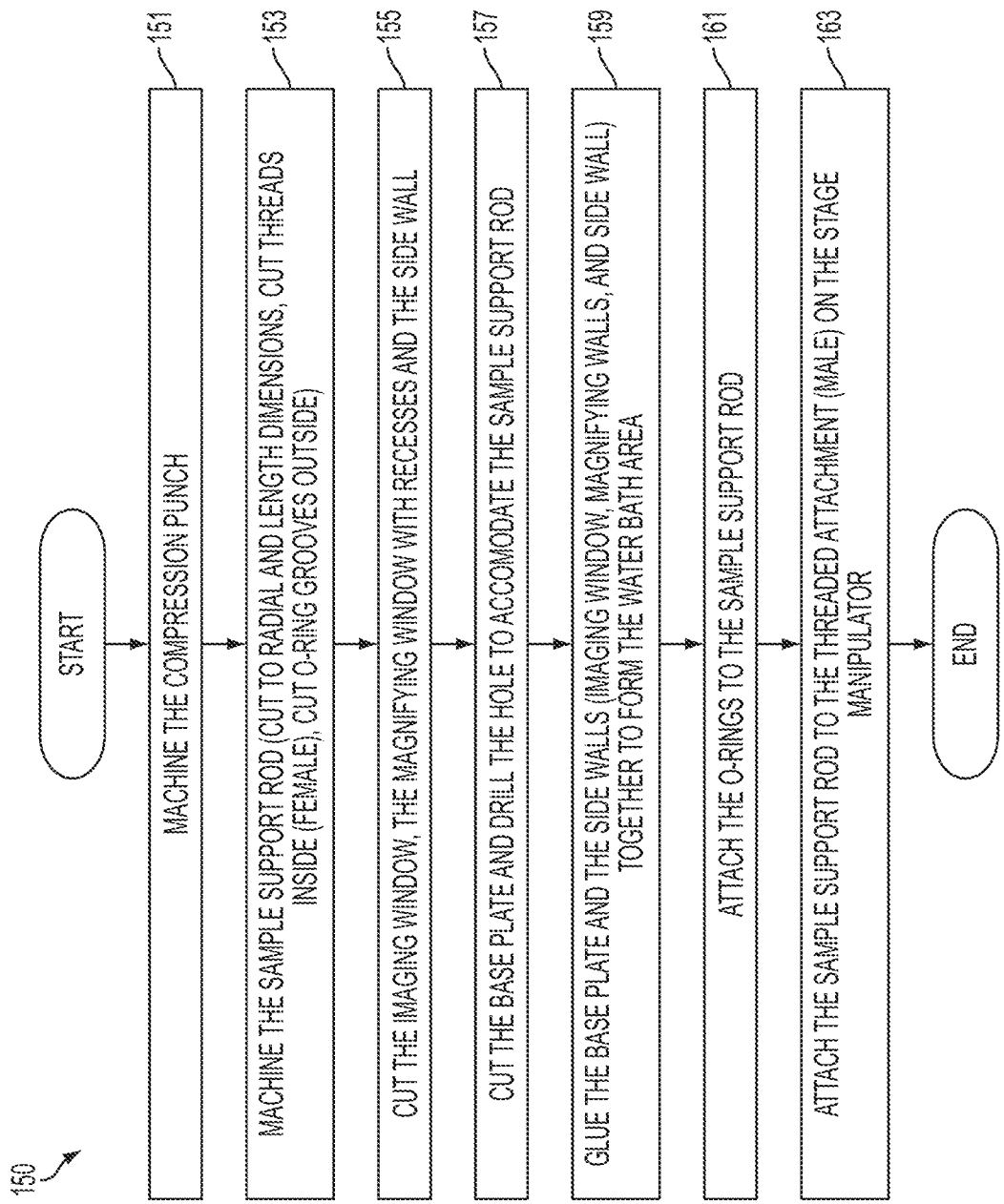
FIG. 8A is a flowchart of the method for assembling the apparatus of the present embodiment.

Referring now primarily to FIG. 8A, method 150 for assembling environmental cell 102 (FIG. 2) can include, but is not limited to including, the steps of preparing two magnifying walls 135, imaging window 103, and side wall 137, machining 151 compression punch 111 (FIG. 1), cutting 153 sample support rod 109 (FIG. 1) to radial and length dimensions and cutting threads inside sample support rod 109 (FIG. 1) and o-ring grooves 113 (FIG. 1) outside, cutting 155 a magnifying window, to mount magnifying lens 107 (FIG. 1), and recesses in magnifying walls 135 (FIG. 3), cutting 157 base plate 101 (FIG. 1) and drilling a hole in base plate 101 (FIG. 1) to accommodate sample support rod 109 (FIG. 1), gluing 159 base plate 101 (FIG. 1) to each of imaging window 103 (FIG. 3), magnifying walls 135 (FIG. 3), and side wall 137 (FIG. 3) to form a water bath area, attaching 161 o-rings 113 (FIG. 1) to the sample support rod 109 (FIG. 1), attaching 163 sample support rod 109 (FIG. 1) to a threaded attachment on a stage manipulator.

Figure 8B:
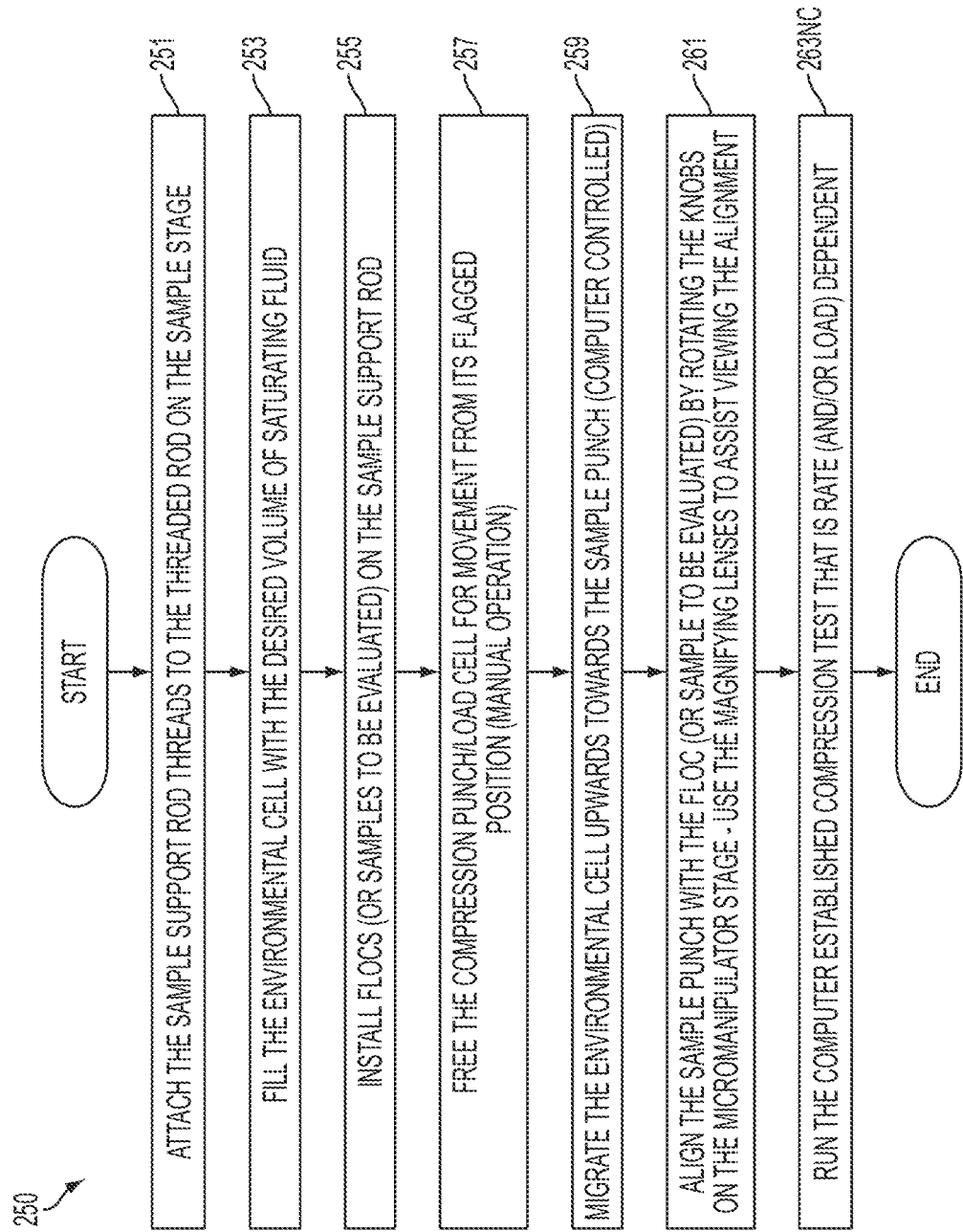
FIG. 8B is a flowchart of the method of collecting compression data using the apparatus of the present embodiment.

Referring now to FIG. 8B, method 250 for collecting compression data on a floc 209 (FIG. 1) can include, but is not limited to including, the steps of attaching 251 threads of sample support rod 109 (FIG. 1) to a threaded rod on a sample stage, sample support rod 109 (FIG. 1) being positioned within environmental cell 102 (FIG. 2), filling 253 environmental cell 102 (FIG. 2) with a preselected volume of saturating fluid, installing 255 samples flocs 209 (FIG. 1) to be evaluated on sample support rod 109 (FIG. 1), if in manual mode, freeing 257 compression punch/load cell 111 (FIG. 1) for movement from its flagged position, if in computer-controlled mode, migrating 259 the environmental cell towards compression punch 111 (FIG. 1), aligning 261 compression punch 111 (FIG. 1) with sample floc 209 (FIG. 1) to be evaluated by rotating knobs on the sample stage using magnifying lens 107 (FIG. 1) associated with environmental cell 102 (FIG. 1) to assist viewing the alignment, and executing 263 a rate/load dependent computer compression test.

Figure 8C:
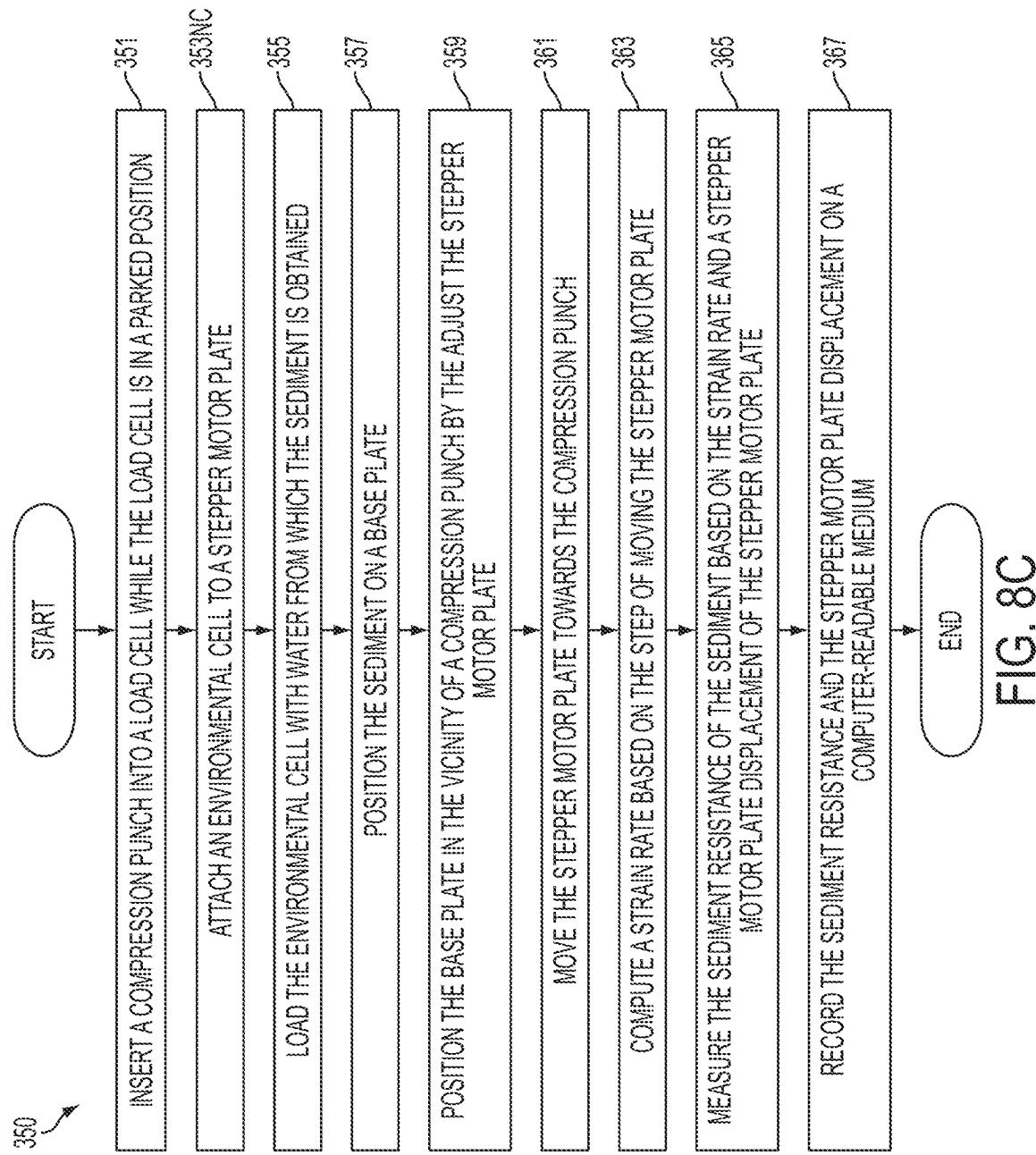
FIG. 8C is a flowchart of the method of testing sediment data using the apparatus of the present embodiment.

Referring primarily to FIG. 8C, method 350 (FIG. 8C) for testing sediment can include, but is not limited to including, the step of inserting 351 (FIG. 8C) compression punch 111 (FIG. 4) into load cell 207 (FIG. 4), while load cell 207 (FIG. 4) is in the a parked position, for example, when flags 206 (FIG. 4) are inserted into load cell 207 (FIG. 4). Method 350 (FIG. 8C) for testing sediment can further include the steps of attaching 353 (FIG. 8C) environmental cell 102 (FIG. 4) to stage mount 219 (FIG. 4) resting atop micromanipulator stage 217 (FIG. 4) that is attached to stepper motor plate 212 (FIG. 4), loading 355 (FIG. 8C) environmental cell 102 (FIG. 4) with the water from which the sediment is obtained, positioning 357 (FIG. 8C) the sediment on base plate 101 (FIG. 1), and positioning 359 (FIG. 8C) the sediment below compression punch 111 (FIG. 4) by adjusting stepper motor plate. Method 350 (FIG. 8C) can still further include the steps of moving 361 (FIG. 8C) the stepper motor plate towards compression punch 111 (FIG. 44), computing 363 (FIG. 8C) a strain rate based on step 361 (FIG. 8C), measuring 365 (FIG. 8C) the sediment resistance of the sediment based on the strain rate and the stepper motor plate displacement, and recording 367 (FIG. 8C) the sediment resistance and the stepper motor plate displacement on a computer-readable medium. Method 350 (FIG. 8C) can optionally include the steps of collecting images of the sediment during the step of moving 361 (FIG. 8C) the stepper motor plate towards compression punch 111 (FIG. 4), and computing any of the compression strength, the Young's modulus, and the elastic modulus of the sediment aggregate based on the sediment resistance and the images. Method 350 (FIG. 8C) can further optionally include the steps of adjusting the stepper motor plate by micromanipulators, and collecting the images through lens side plate 135 (FIG. 3) of environmental cell 102 (FIG. 4). Method 350 (FIG. 8C) can still further optionally include the steps of obtaining the sediment from any of a river, a laboratory, and an ocean bottom, and positioning the sediment on base plate 101 (FIG. 4) using a pipette. Method 350 (FIG. 8C) can even further optionally include the steps of situating magnifying lenses 107 (FIG. 4) at 90° angles to each other, aligning the magnifying lenses until the sediment is in line with compression pin 111 (FIG. 4), and verifying the alignment based on the images.

Referring again primarily to FIGS. 8A and 8B, methods 150 (FIG. 8A) and 250 (FIG. 8B) can be, in whole or in part, implemented electronically. Signals representing actions taken by elements of apparatus 100 (FIG. 1) and other disclosed embodiments can travel over at least one live communications network (connected by communication cables 247 (FIG. 5)). Control and data information can be electronically executed and stored on at least one computer-readable medium accessible by cables 247 (FIG. 5). Apparatus 100 (FIG. 1) can be implemented to communicate with at least one computer node in at least one live communications network. Common forms of at least one computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the at least one computer readable medium can contain graphs in any form including, but not limited to, Graphic Interchange Format (GIF), Joint Photographic Experts Group (JPEG), Portable Network Graphics (PNG), Scalable Vector Graphics (SVG), and Tagged Image File Format (TIFF).

Although the present teachings have been described with respect to various embodiments, it should be realized these teachings are also capable of a wide variety of further and other embodiments.

What is claimed is:

1. A apparatus for characterizing mechanical properties of a sample, comprising:
    a container configured with at least one magnifying port and at least one opening, the container holding a preselected depth of fluid;
    a sample support rod extending from a wall of the container, the sample support rod being configured to hold the sample so that it is submerged in the fluid and positioned based on a magnifying device situated in the at least one magnifying port, the sample support rod being further configured with a mechanical drive forcing the container; and
    a compression punch being positioned at one of the at least one the openings, the compression punch configured with a load cell;
    wherein the sample support rod and the sample interact with the compression punch to generate force and displacement data characterizing the mechanical properties of the sample, the force and displacement data being automatically transferred to a load cell computer by the load cell, the load cell computer automatically translating the force and displacement data into a force-displacement curve indicative of the material properties of the sample.

2. The apparatus according to claim 1, wherein the at least one opening comprises a port for manipulating the sample.

3. The apparatus according to claim 1, wherein the magnifying device comprises a permanently integrated magnifying lens.

4. The apparatus according to claim 1, wherein the magnifying device comprises a temporarily integrated magnifying lens.

5. The apparatus according to claim 1, wherein the magnifying port comprises a camera attachment.

6. The apparatus according to claim 1, wherein the magnifying device comprises a magnifying lens and a camera.

* * * * *